United States Patent
Slowey et al.

(10) Patent No.: US 9,645,091 B2
(45) Date of Patent: May 9, 2017

(54) SPECIMEN SAMPLE COLLECTION DEVICE AND TEST SYSTEM

(75) Inventors: Paul D. Slowey, Vancouver, WA (US);
James Wickstead, Cedar Knolls, NJ (US); Keith Seritella, Washington, NJ (US); Brian Forbes, Sparta, NJ (US); John Ennis, Vancouver, WA (US); Richard Herrig, Phoenix, AZ (US); Jason Giddings, Forest Grove, OR (US); Paul Smith, Washaugal, WA (US)

(73) Assignee: BAMBURGH MARRSH, LLC, Vancouver, WA (US)

( * ) Notice: Subject to any disclaimer, the term of this patent is extended or adjusted under 35 U.S.C. 154(b) by 999 days.

(21) Appl. No.: 13/165,769

(22) Filed: Jun. 21, 2011

(65) Prior Publication Data

US 2012/0282154 A1    Nov. 8, 2012

Related U.S. Application Data

(63) Continuation-in-part of application No. 11/454,214, filed on Jun. 15, 2006, now abandoned, and a continuation-in-part of application No. 13/031,978, filed on Feb. 22, 2011, now Pat. No. 8,273,305, which is a continuation of application No. 11/827,898, filed on Jul. 14, 2007, now Pat. No. 7,927,548, which is a continuation-in-part of application No. 11/045,180, filed on Jan. 27, 2005, now Pat. No. 7,618,591, application No. 13/165,769, which is a continuation-in-part of application No. 12/419,939, filed on Apr. 7, 2009, now Pat. No. 8,025,851.

(60) Provisional application No. 60/691,330, filed on Jun. 16, 2005, provisional application No. 60/630,613, filed on Nov. 23, 2004, provisional application No. 60/539,929, filed on Jan. 28, 2004, provisional application No. 61/123,378, filed on Apr. 7, 2008.

(51) Int. Cl.
*G01N 21/75* (2006.01)
*G01N 21/84* (2006.01)

(52) U.S. Cl.
CPC .  *G01N 21/8483* (2013.01); *G01N 2201/0221* (2013.01); *Y10T 436/11* (2015.01)

(58) Field of Classification Search
None
See application file for complete search history.

(56) References Cited

U.S. PATENT DOCUMENTS

| | | | |
|---|---|---|---|
| 6,168,957 B1 * | 1/2001 | Matzinger et al. | 436/518 |
| 6,478,939 B1 * | 11/2002 | Lennox et al. | 204/403.08 |
| 6,514,460 B1 * | 2/2003 | Fendrock | 422/404 |
| 7,267,799 B1 * | 9/2007 | Borich et al. | 422/82.05 |
| 2001/0016800 A1 * | 8/2001 | Koh et al. | 702/188 |
| 2005/0182358 A1 * | 8/2005 | Veit et al. | 604/93.01 |

* cited by examiner

*Primary Examiner* — Neil N Turk
(74) *Attorney, Agent, or Firm* — Mark E. Beatty; Kurt M. Rylander; Rylander & Associates PC

(57) ABSTRACT

A portable, hand-held electro-optical reader and specimen sample collector is provided, including an absorbent pad, one or more test strips contained in the collector handle to provide observable results through a window, the handle insertable into the reader for immediate recording and analysis. The system includes means to automatically provide subject and test specific data with the test results and retain samples for later verification analysis.

1 Claim, 15 Drawing Sheets

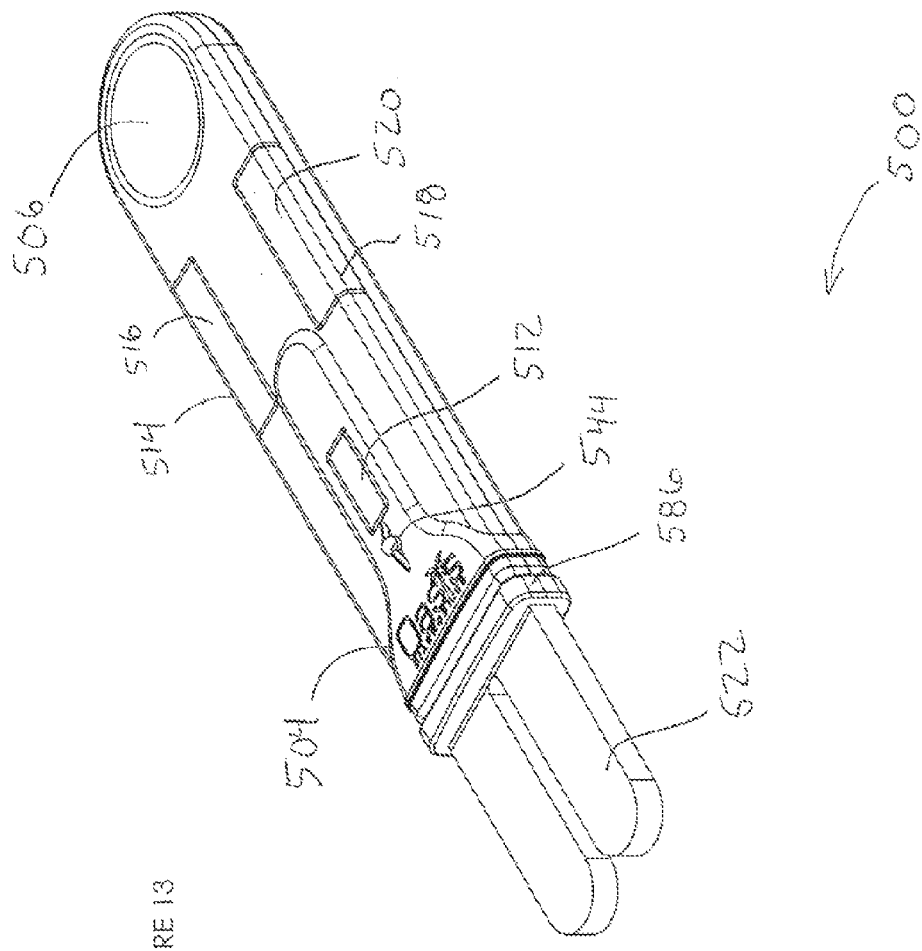
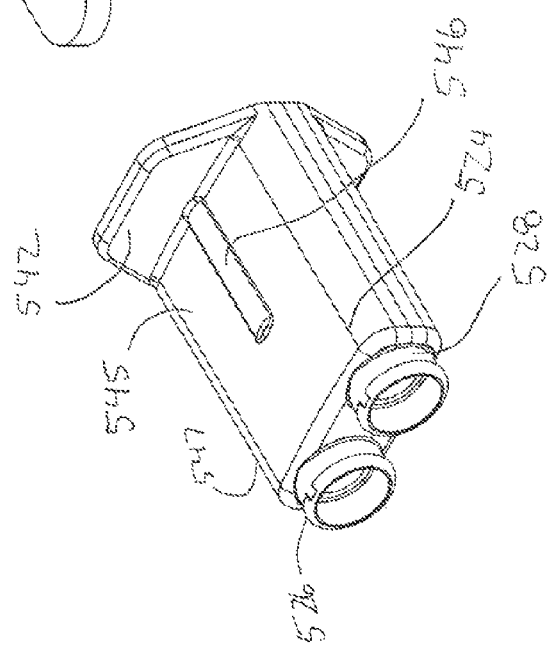
FIGURE 13

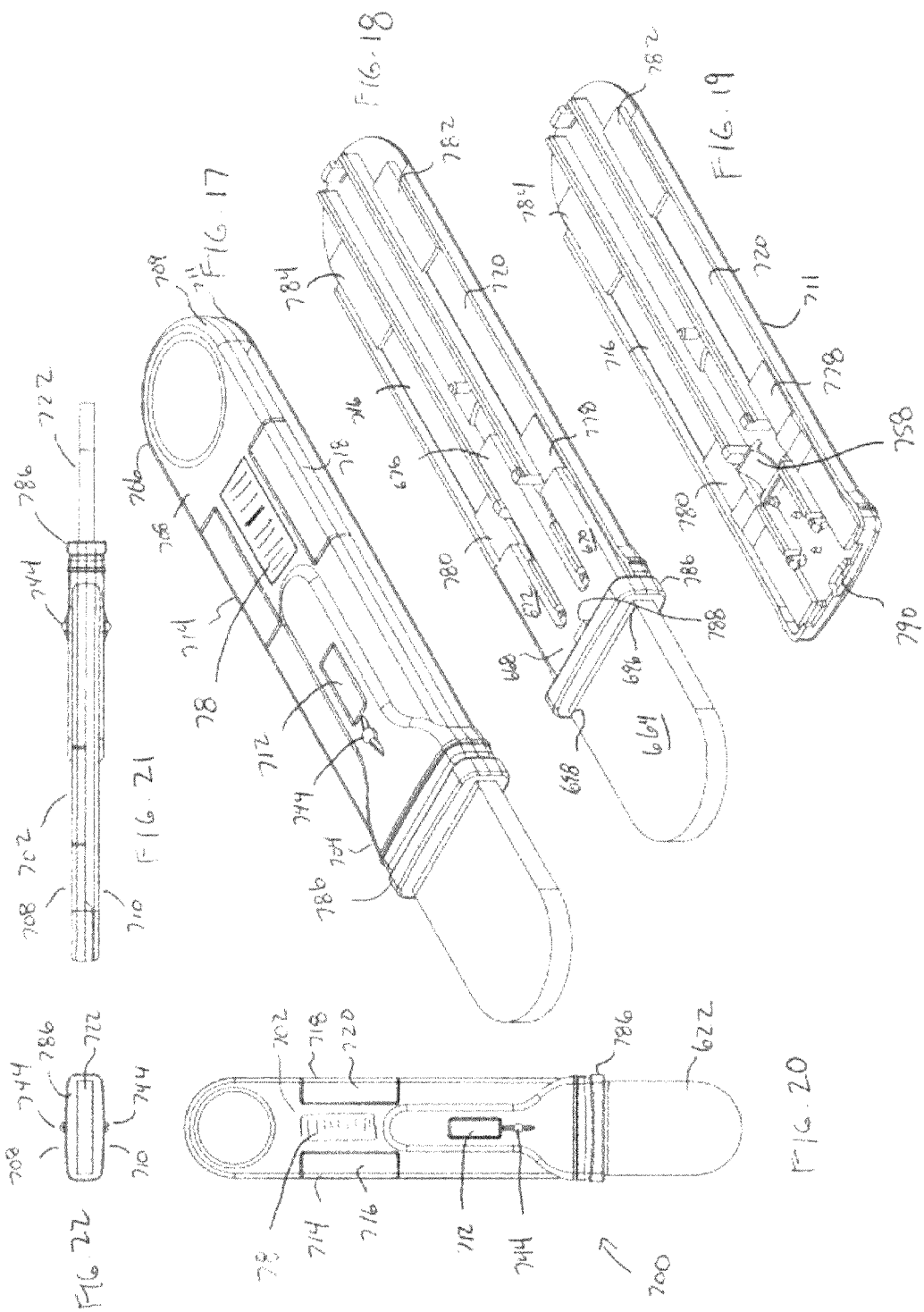

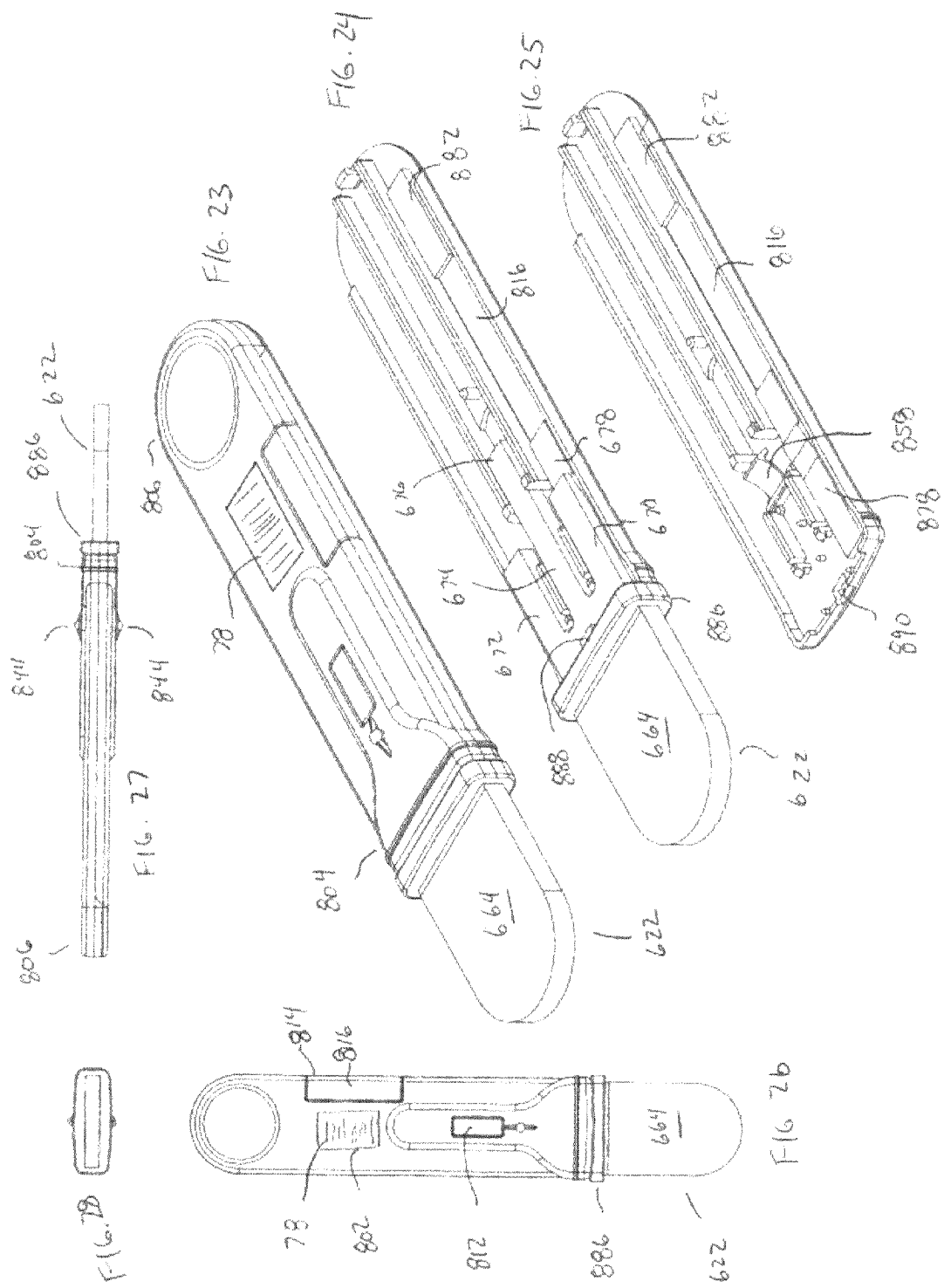

SPECIMEN SAMPLE COLLECTION DEVICE AND TEST SYSTEM

CROSS-REFERENCE TO RELATED APPLICATION

This application is a continuation-in-part of, and claims priority to, the following applications, the disclosures of each of which are hereby incorporated into this Application by reference: co-pending U.S. Nonprovisional application Ser. No. 11/454,214 filed Dec. 28, 2006, which is a nonprovisional application of U.S. Provisional Application Ser. No. 60/691,330 filed Jun. 16, 2005; co-pending U.S. Nonprovisional application Ser. No. 13/031,978 filed Feb. 22, 2011, which is a continuation of U.S. Nonprovisional application Ser. No. 11/827,898 filed Jul. 14, 2007, which is a continuation-in-part of U.S. Nonprovisional application Ser. No. 11/045,180 filed Jan. 27, 2005 (issued as U.S. Pat. No. 7,618,591) which is a nonprovisional of U.S. Provisional Application Ser. Nos. 60/630,613 filed Nov. 23, 2004 and 60/539,929 filed Jan. 28, 2004; and, co-pending U.S. Nonprovisional application Ser. No. 12/419,939 filed Apr. 7, 2009, which is a nonprovisional of U.S. Provisional Application Ser. No. 61/123,378 filed Apr. 7, 2008.

FIELD OF THE INVENTION

The present invention relates to body fluid sample collection and test systems, and more particularly to hand-portable apparatus and methods for imaging, analyzing and recording the tests and transferring the analysis and images to remote facilities and/or printers.

BACKGROUND

On-site screening and testing for drugs of abuse and other substances requires small, highly automated, hand-held devices which can be used in the field or within a workplace. Such test devices are typically used in law enforcement situations, for example, where testing for drugs of abuse can be administered roadside. They are also used in workplace screening and testing, to mention just a few. Such circumstances require that such devices be rugged, easy to use, battery powered with sufficient battery life, and capable of printing test results to a remote printer preferably using wireless transmission. It is also important that a person conducting such a test be able to enter information about himself (herself) and about the individual undergoing testing. This information may include date and time, driver's license number, social security, green card or other data. Ideally, this information also provides a record of the actual test for further proof and validation. The data and test information should be electronically stored to facilitate later transfer to a PC or other computer for formal record keeping. The device must be capable of reading and recording test collectors, thereby removing the subjectivity of the user while also providing information and documentation to substantiate the results. This substantiation should come in the form of electronic data which eliminates transposition errors and provides visual and electronic records of the specific test as well as a printed test result.

In response to the industry's needs, although manufacturers have developed drug screening systems, none have successfully addressed the above requirements for a portable, field usable device which clearly and concisely links the specific test to the individual conducting the test and the person being tested. This linking and substantiation is essential for a legal document and for use in the criminal justice system where chain of custody verification is critical.

Thus, there is a need for a rugged, hand-portable system that provides the ability to quickly, safely and sanitarily obtain a body fluid sample, especially saliva, test the sample for the indications of target substances with immediate results, retain original sample fluids for later verification testing and for more extensive test regimes, detect and record the test-specific data electronically along with patient and collector identifying data, and transmit the data to a location remote from the test site over a communications network.

SUMMARY AND ADVANTAGES

A sample collection device and test system includes an electro-optical reader and a sample collector having an absorbent pad to receive a sample and a test strip in fluid communication with the absorbent pad and contained within the collector handle to insert into the reader for recording and analysis. The sample collector includes a pad compression tube sealingly matable to a sample collection tube, and a progressive locking mechanism. The sample collector includes a collector dam to seal against the pad compression tube and the pad. A reader includes a receiving port to receive a sample collector, an imaging device, a data handling device, and associated controls, and a printer to provide immediate hard copies of results. The reader and sample collector provide for numerous configurations and flexibility.

The system of the present invention presents numerous advantages, including: (1) compact hand-portable design; (2) rapid test results with immediate verification ability; (3) retention of sample fluids for confirmation or more extensive lab testing; (4) low cost; (5) reliable indication of sample volume sufficiency; (6) the ability to test for multiple markers of a given condition with a single rapid sample, increasing reliability and efficiency of testing; (7) the ability to perform large scale screening testing on a large population; (8) the ability to perform reliable testing in field conditions.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

FIG. 13 is a perspective view of a double-tongue, multiple-test strip sample collector of an embodiment.

FIG. 17 is a perspective view of a single-tongue multi-test strip collector of an embodiment.

FIG. 18 is a partially disassembled view of a single-tongue multi-test strip collector of an embodiment.

FIG. 19 is a partially disassembled view of a single-tongue multi-test strip collector of an embodiment.

FIG. 20 is a plan view of a single-tongue multi-test strip collector of an embodiment.

FIG. 21 is a side view of a single-tongue multi-test strip collector of an embodiment.

FIG. 22 is an end view of a single-tongue multi-test strip collector of an embodiment.

FIG. 23 is a perspective view of a single-tongue single-test strip collector of an embodiment.

FIG. 24 is a partially disassembled view of a single-tongue single-test strip collector of an embodiment.

FIG. 25 is a partially disassembled view of a single-tongue single-test strip collector of an embodiment.

FIG. 26 is plan view of a single-tongue single-test strip collector of an embodiment.

FIG. 27 is a side view of a single-tongue single-test strip collector of an embodiment.

FIG. 28 is and end view of a single-tongue single-test strip collector of an embodiment.

DETAILED DESCRIPTION

Figure 1:
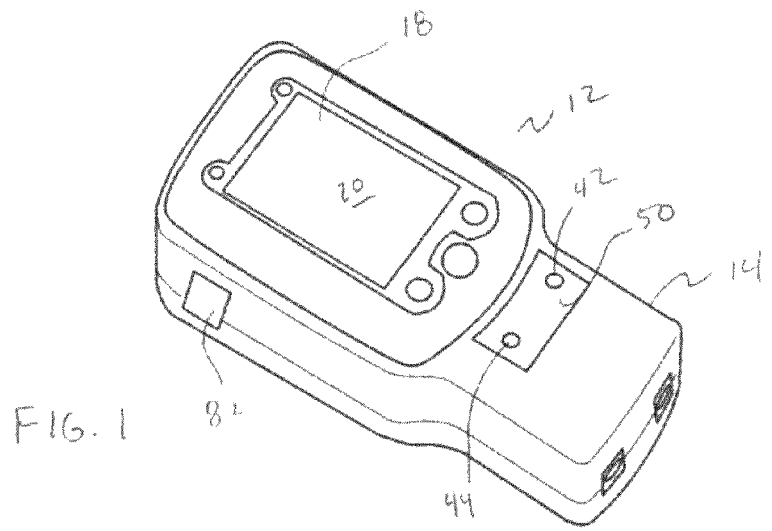
FIG. 1 is a left-side perspective view of a first embodiment of an electro-optical reader.
Figure 2:
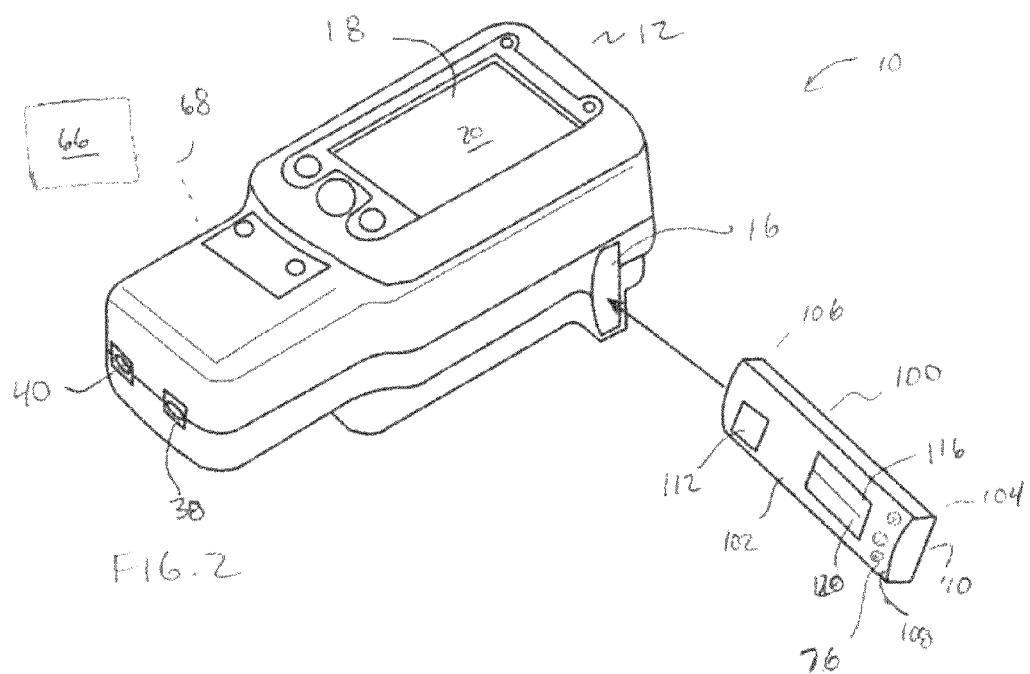
FIG. 2 is a right-side perspective view of a first embodiment of an electro-optical reader and sample collector.
Figure 3:
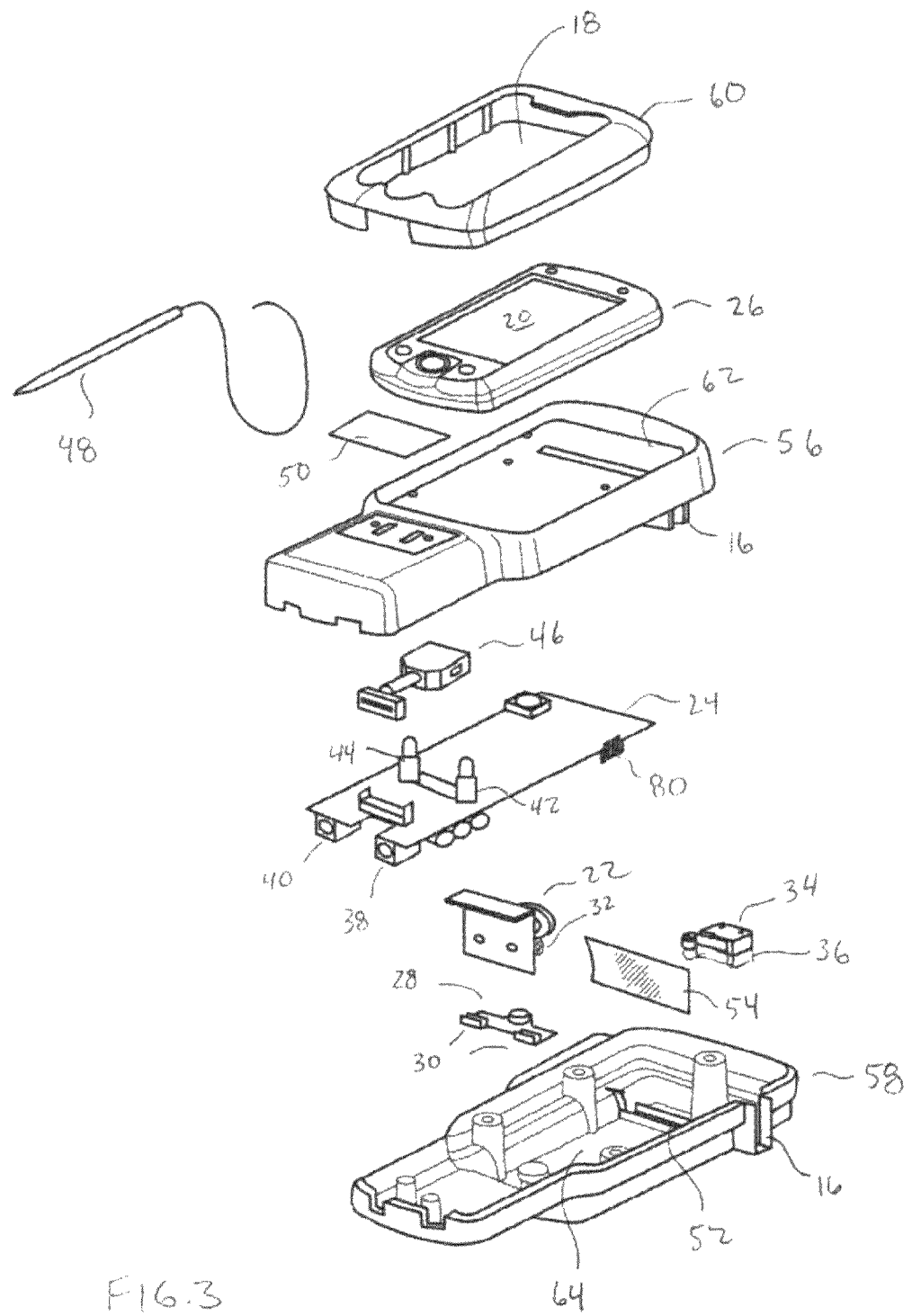
FIG. 3 is an exploded view of a first embodiment of an electro-optical reader.

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

A specimen sample collection and test system includes a saliva sample collector and electro-optical reader, the sample collector including: a handle having opposing first and second ends and opposing first and second sides, a sufficiency indicator, and a window to observe indications from a test strip; an absorbent pad partially contained within the handle and extending out from the handle first end; a pad compression tube insertable over the absorbent pad and around the first end of the handle, the pad compression tube including one or more collection tube ports to receive a collection tube, wherein the window remains unobscured when the pad compression tube is fully inserted over the handle first end; one or more test strips contained within the handle in fluid communication with the absorbent pad, the one or more test strips to detect a substance and produce an observable indication through the window in the handle; and, the electro-optical reader including a sample collector port to receive the handle second end at least up to and including the window, the electro-optical reader to detect the observable indication through the window and record the result.

A specimen sample collection and test system may include a progressive locking mechanism having a first part disposed on the handle and a second part disposed on the pad compression tube, to resist separation of a pad compression tube inserted over the absorbent pad and around the handle first end.

A specimen sample collection and test system may include the handle having first and second projections disposed on first and second handle sides, respectively; and, the pad compression tube including opposing first and second channels extending lengthwise along opposing pad compression tube side walls to frictionally engage the first and second projections, respectively.

A specimen sample collection and test system may include the handle having first and second unidirectional locking teeth disposed on the handle first and second sides, respectively; and, the pad compression tube including a plurality of locking holes on opposing sides of the pad compression tube to lockingly engage the locking teeth, the locking holes spaced apart lengthwise on the pad compression tube to lock the pad compression tube over the handle first end in progressively tighter compression positions.

A specimen sample collection and test system may include a collection tube sealingly connectable to at least one of the pad compression tube one or more collection tube ports, the collection tube including one or more sample chambers, wherein when the collection tube is connected to the pad compression tube at least one of the corresponding one or more sample chambers is in fluid communication with the pad compression tube and the absorbent pad.

A specimen sample collection and test system may include a plurality of alternating lands and grooves disposed on the interior wall of the pad compression tube proximal to the collection tube ports, the grooves in fluid communication with the collection tube ports.

A specimen sample collection and test system may include a collector dam insertable over the absorbent pad against the handle first end, the collector dam in sealing contact with the absorbent pad and the inside wall surface of the pad compression tube, and wherein the collector dam permits liquid sample to migrate along the absorbent pad during collection, but prevents flow when the absorbent pad and handle are inserted into the pad compression tube.

A specimen sample collection and test system may include wherein the electro-optical reader further includes a housing having an aperture to view and operate a programmable data handling device touch screen; an imaging device mounted within the housing and having a field of view oriented to image a selected portion of a sample collector handle inserted into the sample collector port; an imaging processor mounted within the housing and in electronic communication with the imaging device and data handing device, the imaging processor to at least receive imaging data from the imaging device, process the imaging data for use by the data handing device, and transmit the imaging data to the data handling device; a programmable data handling device removably mounted within the housing, the data handling device including a touch screen, wherein the touch screen is aligned with the housing aperture when mounted within the housing.

A specimen sample collection and test system may include a mechanically adjustable mounting to receive and retain the imaging device within the housing and align the imaging device field of view.

A specimen sample collection and test system may include wherein the programmable data handling device is a self-contained unit.

A specimen sample collection and test system may include collector identification indicia disposed on the sample collector handle so as to be received within the sample collector port when the sample collector handle is inserted into the collector port; and, the reader including collector identification indicia sensing means.

A specimen sample collection and test system may include wherein the collector identification indicia includes a plurality of color markings.

A specimen sample collection and test system may include the collector identification indicia sensing means including one or more electro-mechanical switches to be selectively actuated by corresponding structures on a sample collector handle.

A specimen sample collection and test system may include the reader further having a sample collector presence detector to detect a sample collector handle inserted into the receiving portion.

A specimen sample collection and test system may include wherein the presence detector includes an electro-mechanical switch.

A specimen sample collection and test system may include wherein the presence detector includes an optical switch.

A specimen sample collection and test system may include wherein the presence detector includes an electro-magnetic switch.

A specimen sample collection and test system may include an optical target disposed on the sample collector to be within the imaging device field of view when the sample collector handle is inserted into the receiving portion.

A specimen sample collection and test system may include wherein the sample collector includes an area on the handle proximal to the window to receive a optical data label, such that the optical data label is within the imaging device field of view when the sample collector handle is inserted into the sample collector port, the optical data to include sample-specific data.

A specimen sample collection and test system may include the sample collector including optical data indicia identifying the sample collector, such that the optical data indicia is within the imaging device field of view when the sample collector handle is inserted into the sample collector port.

A specimen sample collection and test system may include a light source mounted within the housing and oriented to illuminate the portion of a sample collector handle inserted within the sample collector port, the light source selectively activatable to illuminate the handle during imaging.

A specimen sample collection and test system may include a light source mounted within the housing and oriented to illuminate a sample collector handle inserted within the sample collector receiving port, the light source selectively activatable by an electronic signal from the imaging processor.

A specimen sample collection and test system may include a lens element disposed between the sample collector port and the imaging device.

A specimen sample collection and test system may include an optical filter disposed between the sample collector port and the imaging device.

A specimen sample collection and test system may include wherein the optical filter is a polarizing filter.

A specimen sample collection and test system may include a shield within the housing disposed between the sample collector receiving port interior cavity portion and the main housing interior cavity portion.

A specimen sample collection and test system may include wherein the data handling device includes wireless communication means to transmit and receive data.

A specimen sample collection and test system may include a printer in electronic communication with the data handling device.

A specimen sample collection and test system may include wherein the printer is mounted within the housing.

A specimen sample collection and test system may include a selectively activated light source directed outwardly through the sample collector port.

A specimen sample collection and test system may include the collector port illuminator to be deactivated by a signal from the collector presence detector.

A specimen sample collection and test system may include at least one test strip including a control line extending transversely across the test strip and one or more indicator lines each disposed at a predetermined distance downstream from the control line.

A specimen sample collection and test system may include wherein the one or more test strips comprise first and second test strips, each test strip in fluid communication with the absorbent pad.

A specimen sample collection and test system may include the first and second test strips each to detect the presence of at least one substance in common in a sample.

A specimen sample collection and test system may include the first and second test strips each to detect the presence of different substances in a sample.

A specimen sample collection and test system may include the first and second test strips each to detect the presence of a different substance in a sample, the different substances each correlating to the same condition of a test subject.

A specimen sample collection and test system may include one or more membranes contained within the handle, each of the one or more membranes corresponding to a test strip and in fluid communication with the absorbent pad and the corresponding test strip.

A specimen sample collection and test system may include a membrane in the handle; and, the one or more test strips including at least one single analyte test strip; wherein the absorbent pad is in fluid communication with the single analyte test strip through the membrane.

A specimen sample collection and test system may include a plurality of test strips in the handle; and, a plurality of membranes in the handle, each membrane corresponding to a single test strip; wherein the absorbent pad is in fluid communication with each of the plurality of test strips through its corresponding membrane.

A specimen sample collection and test system may include a plurality of analyte test strips in the handle; and, a single membrane in the handle; wherein the absorbent pad is in fluid communication with each of the test strips through the membrane.

A specimen sample collection and test system may include wherein the absorbent pad is split, divided into two parts and connected at a base of the absorbent pad.

A specimen sample collection and test system may include wherein the sufficiency indicator is a light pipe.

A specimen sample collection and test system may include wherein the light pipe further includes: a first end surface with a marking, and a second surface in physical contact with the absorbent pad creating a refractive boundary, wherein the second surface is oriented at an angle of incidence to the first surface such that when the absorbent pad absorbs a sufficient liquid sample the refractive properties of the boundary alter the observability of the mark.

A specimen sample collection and test system may include a spacer contained within the handle, the spacer disposed between the absorbent pad and the handle structure to urge the absorbent pad against the light pipe second surface.

A specimen sample collection device and test system includes an electro-optical reader to receive a sample collector, the electro-optical reader further comprising: a housing including an aperture to view and operate a programmable data handling device touch screen, and a sample collector port to receive a portion of a sample collector having one or more test strips to produce observable indications of the presence of selected substances within a test sample; an imaging device mounted within the housing and having a field of view oriented to image a selected portion of the sample collector inserted into the sample collector port; an imaging processor mounted within the housing and in electronic communication with the imaging device and data handing device, the imaging processor to at least receive imaging data from the imaging device, process the imaging data for use by the data handing device, and transmit the imaging data to the data handling device; a programmable data handling device removably mounted within the housing, the data handling device including a touch screen, wherein the touch screen is aligned with the housing aperture when mounted within the housing.

A test system reader may include a mechanically adjustable mounting to receive and retain the imaging device within the housing and align the imaging device field of view.

A test system reader may include wherein the programmable data handling device is a self-contained unit.

A test system reader may include sample collector identification means to identify the type of collector received within the sample collector port when a sample collector handle is inserted into the sample collector port.

A test system reader may include a sample collector presence detector to detect a sample collector inserted into the collector port.

A test system reader may include the presence detector comprising an electro-mechanical switch.

A test system reader may include the presence detector comprising an optical switch.

A test system reader may include the presence detector comprising an electro-magnetic switch.

A test system reader may include detection means to detect an optical target disposed on a sample collector to be within the imaging device field of view when the sample collector handle is inserted into the receiving portion, the optical target to provide a reference to electronically adjust the orientation of an image received by the imaging device.

A test system reader may include means to receive, record, and interpret an optical data label placed on a sample collector proximal to the test strip window, such that the optical data label is within the imaging device field of view when the sample collector handle is inserted into the sample collector port, the optical data to include sample-specific data.

A test system reader may include means to receive, record, and interpret optical data indicia identifying the sample collector, the optical data indicia disposed within the imaging device field of view when the sample collector handle is inserted into the sample collector port.

A test system reader may include a light source mounted within the housing and oriented to illuminate the portion of a sample collector handle inserted within the sample collector port, the light source selectively activatable to illuminate the handle during imaging.

A test system reader may include a light source mounted within the housing and oriented to illuminate a sample collector handle inserted within the sample collector receiving port, the light source selectively activatable by an electronic signal from the imaging processor.

A test system reader may include a lens element disposed between the sample collector port and the imaging device.

A test system reader may include an optical filter disposed between the sample collector port and the imaging device.

A test system reader may include wherein the optical filter is a polarizing filter.

A test system reader may include a shield within the housing disposed between the sample collector receiving port interior and housing interior.

A test system reader may include wireless communication means to transmit and receive data.

A test system reader may include a printer in electronic communication with the data handling device.

A test system reader may include a printer mounted within the housing.

A test system reader may include a selectively activated light source directed outwardly through the sample collector port.

A test system reader may include collector port illuminator to be deactivated by a signal from the collector presence detector.

Referring to FIGS. 1-7, a first embodiment of a specimen sample collection device and test system 10 is shown. In the embodiment, a test system 10 includes a saliva sample collector 100 and electro-optical reader 12. Sample collector includes a handle 102 having opposing first and second ends 104, 106, respectively, and opposing first and second sides 108, 110, respectively, a sufficiency indicator 112, and a window 114 to observe indications from a test strip 116; an absorbent pad 122 partially contained within the handle 102 and extending out from the handle first end 104; a pad compression tube 124 insertable over the absorbent pad 122 and around the first end 104 of the handle 102, the pad compression tube 124 including one or more collection tube ports 126, 128, to receive a collection tube 130, wherein the window 114 remains unobscured when the pad compression tube 124 is fully inserted over the handle first end 104; one or more test strips 116, 120 contained within the handle 102 in fluid communication with the absorbent pad 122, the one or more test strips 116, 120 to detect a substance and produce an observable indication through the window 114 in the handle 102; and, the electro-optical reader 12 including a sample collector receiving portion 16 to receive the handle second end 106 at least up to and including the window 114, the electro-optical reader 12 to detect the observable indication through the window 114 and record the result. In the embodiment, second test strip 120 is observable through second window 118, and both first and second windows 114, 118 are located on handle first side 108, so that both will be in the field of view of the reader imaging device 22. Pad compression tube 124 includes first and second collection tube ports 126, 128, sealingly connectable to a collection tube 130 having first and second sample chambers 132, 134, such that when collection tube 130 is coupled to pad compression tube 124, each of sample chambers 132, 134 is in fluid communication with a corresponding collection tube port 126, 128, respectively. Sealing cap 136 is provided to seal an expressed sample in collection tube 130. Pad compression tube 124 is provided with removable seals 138 and 140 to maintain cleanliness until needed for use. Pad compression tube 124 includes a flange 142 to assist in gripping while compressing an absorbent pad.

Figure 8:
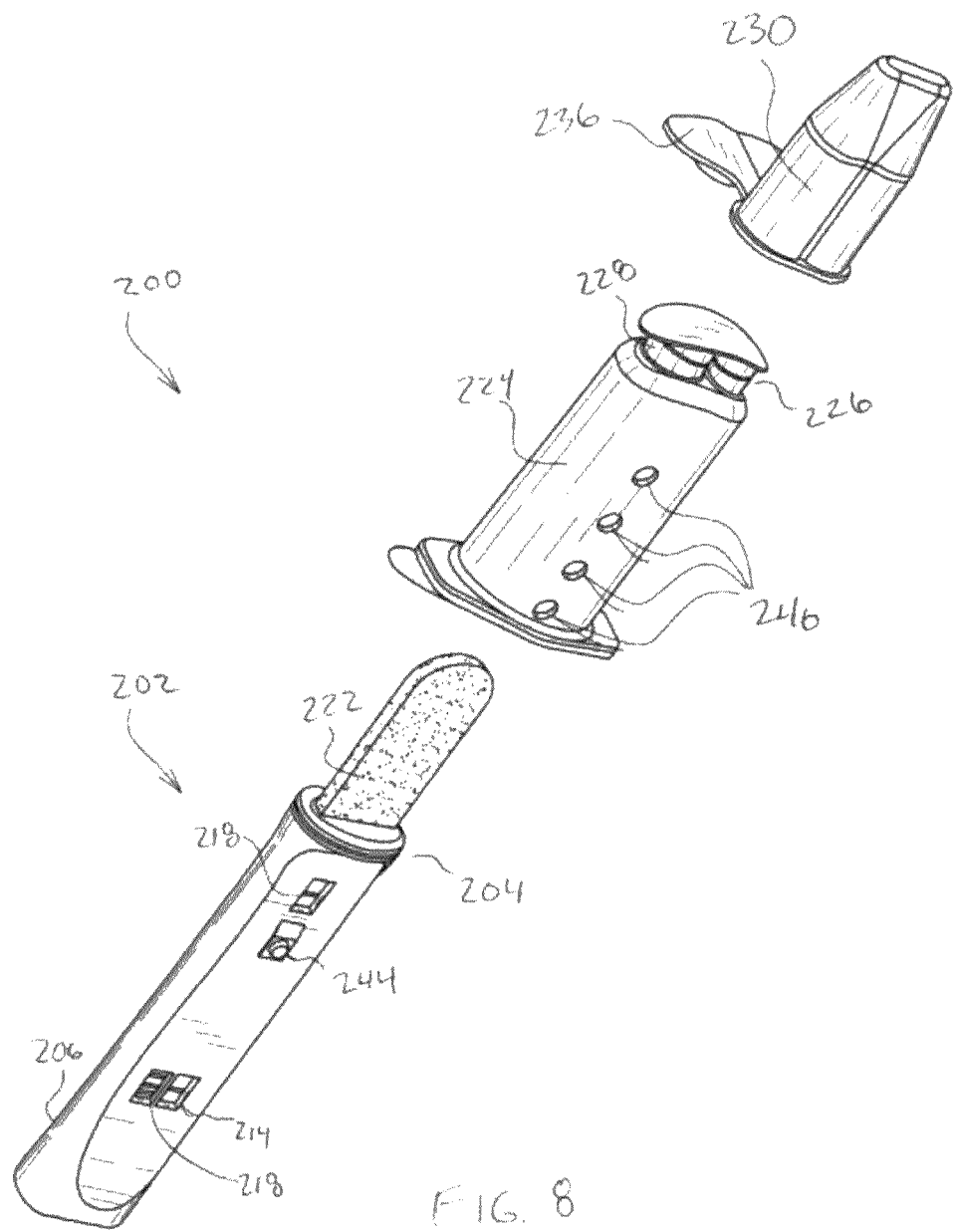
FIG. 8 is a view of a sample collector of a second embodiment.

Referring to FIG. 8, in a second embodiment of a sample collector 200, a progressive locking mechanism is provided having a first part 244 disposed on the handle 202 and a second part 246 disposed on the pad compression tube 224, to resist separation of a pad compression tube 224 inserted over the absorbent pad 222 and around the handle first end 204. In the embodiment, locking mechanism first part 244 includes unidirectional locking teeth 244 disposed on the first and second sides 108, 110, respectively to engage the plurality of locking holes 246 disposed lengthwise along opposing sides of pad compression tube 224. In the embodiment, sample collector 200 includes handle 202 having opposing first and second ends 204, 206, an absorbent pad 222 partially contained with handle 202, a sufficiency indicator 212 in handle 202, and first and second windows 214, 218, to observe indications from test strips contained in handle 202. Collection tube 230 is provided to sealingly mate to collection tube ports 226 and 228 on pad compression tube 224.

Figure 9:
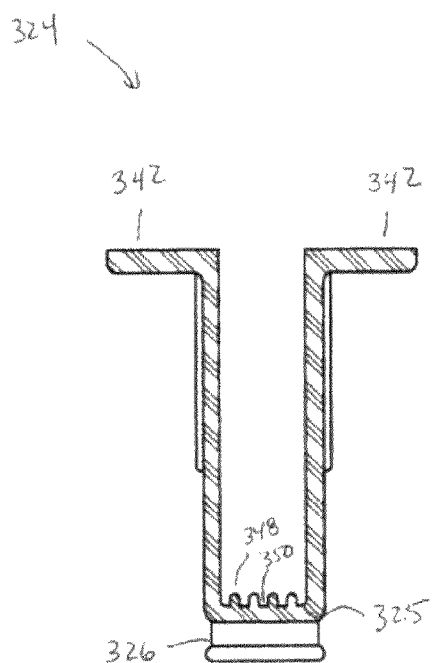
FIG. 9 is a cutaway side view of a pad compression tube of a first embodiment.
Figure 9A:
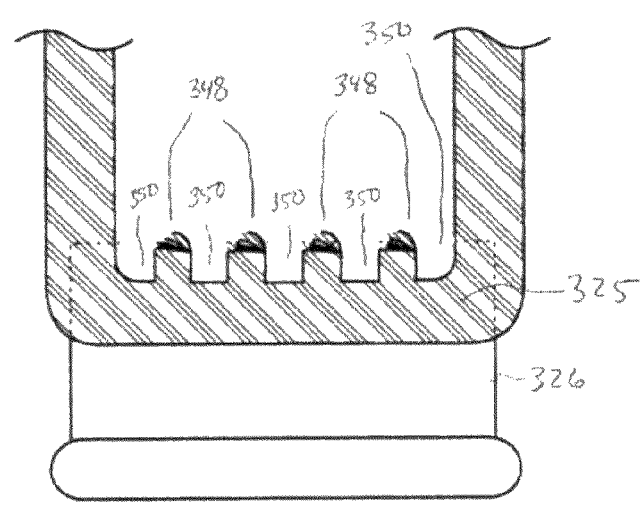
FIG. 9A is a close up cutaway side view of a pad compression tube of a first embodiment.

Referring to FIGS. 9 and 9A, the interior of a pad compression tube 324 of a third embodiment includes alternating lands 348 and grooves 350 disposed on the interior of the end wall 325 proximal to collection tube ports 326 and 328 (not visible in the view). Grooves 350 are in fluid communication with collection tube ports 326, 328. The lands and grooves 348, 350, provide a setoff and drain path to permit expressed sample to flow to the collection tube ports 326, 328, and prevent the absorbent pad from plugging the collection tube ports 326, 328.

Figure 10:
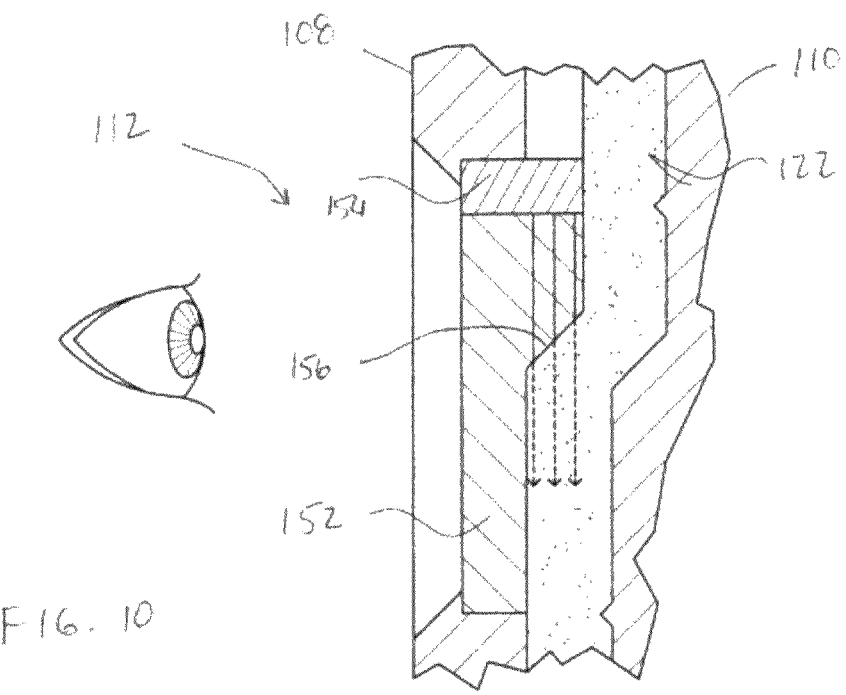
FIG. 10 is a view of a light pipe sufficiency indicator with a saturated pad.
Figure 11:
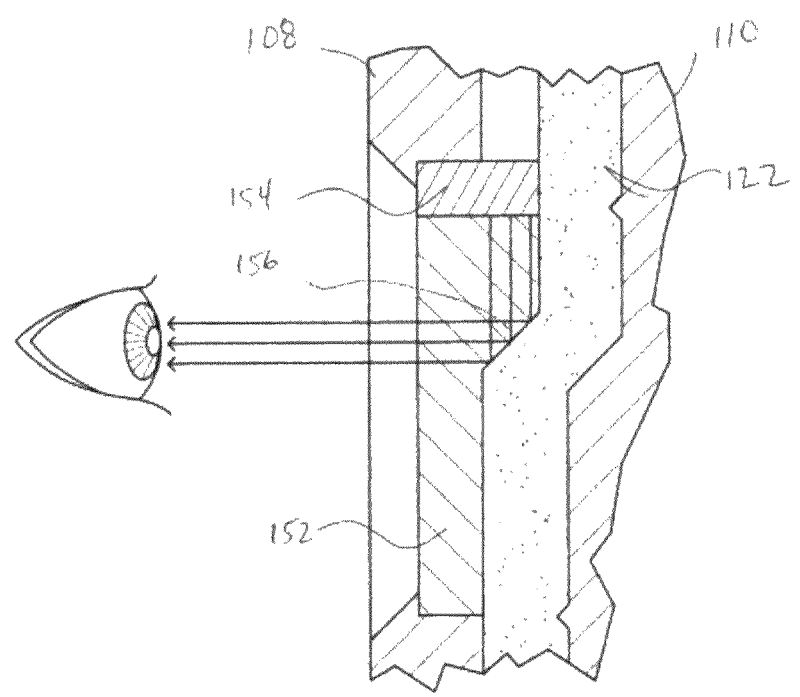
FIG. 11 is a view of a light pipe sufficiency indicator with a dry pad.

Referring to FIGS. 10 and 11, a sample adequacy indicator 112 of a sample collector 100 of the first embodiment is shown. In the embodiment, sample adequacy indicator 112 is a light pipe 152 having a first surface 154 with a marking and a second surface 156 at an angle of incidence to the first surface 154 and in contact with absorbent pad 122 to create a refraction boundary. When the pad 122 is not saturated, as in FIG. 15, the refractive property of the boundary 156 causes most of the light to refract up toward the observer so that the mark 154 is visible to the observer. When the pad 122 is saturated with sample, for example saliva, as in FIG. 14, the refractive properties of boundary 156 change, so that less light is refracted up toward the observer, and the marked surface 154 is no longer visible. The mark on surface 154 could be a design, a color coating, or could simply be the interior surface of handle first part 108 abutting first surface 154, which is equivalent to coating the surface.

Figure 12:
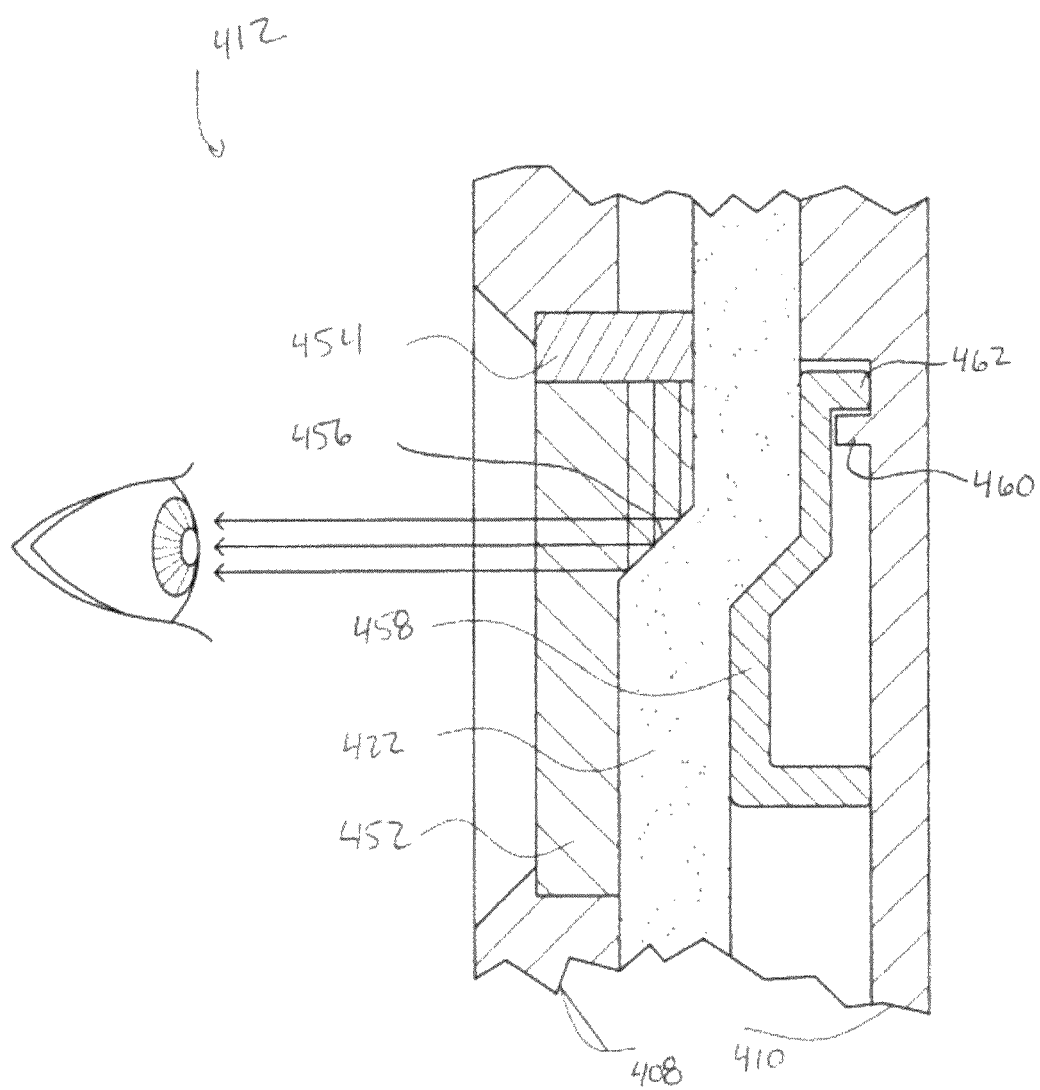
FIG. 12 is a view of a light pipe sufficiency indicator with a dry pad and a spacer.
Figure 16:
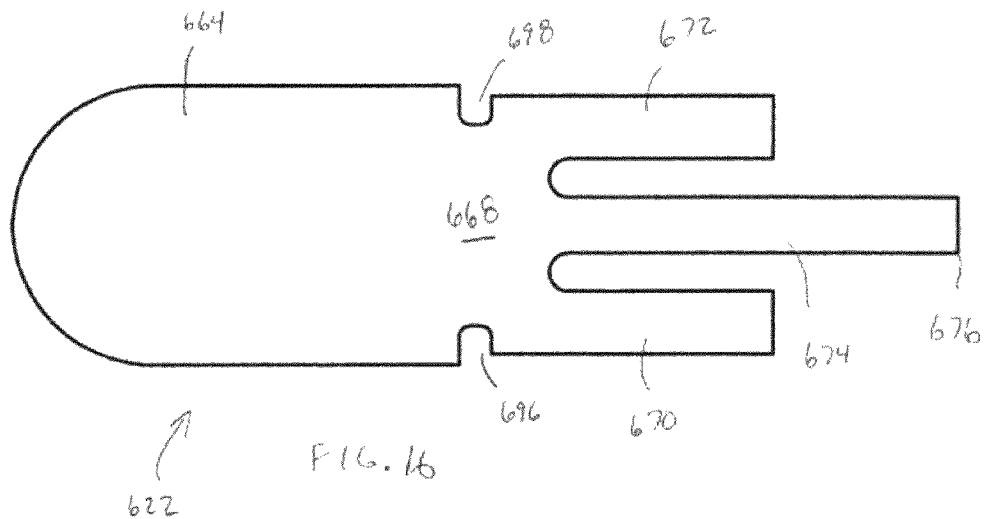
FIG. 16 is a plan view of a single-tongue absorbent pad of an embodiment.

Referring to FIG. 12, a sample adequacy indicator 412 of a sample collector 400 of a fourth embodiment is shown. In the embodiment, sample adequacy indicator 412 is a light pipe 452 having a first surface 454 with a marking and a second surface 456 at an angle of incidence to the first surface 454 and in contact with absorbent pad 422 to create a refraction boundary. When the pad 422 is not saturated, as in FIG. 16, the refractive property of the boundary 456 causes most of the light to refract up toward the observer so that the mark 454 is visible to the observer. When the pad 422 is saturated with sample, for example saliva, the refractive properties of boundary 456 change, so that less light is refracted up toward the observer, and the marked surface 454 is no longer visible. The mark on surface 454 could be a design, a color coating, or could simply be the interior surface of handle first part 408 abutting first surface 454, which is equivalent to coating the surface. In the embodiment, spacer 458 is contained within the handle 402, the spacer 458 disposed between the absorbent pad 422 and the handle structure 410 to urge the absorbent pad 422 against the light pipe second surface 456. Spacer 458 includes a lip 462 which fits into groove 460 to retain spacer 458 in place. The surface contour of spacer 456 substantially conforms to the surface contour of second surface 456 to ensure pad 422 maintains continuous contact with second surface 456.

Figure 5:
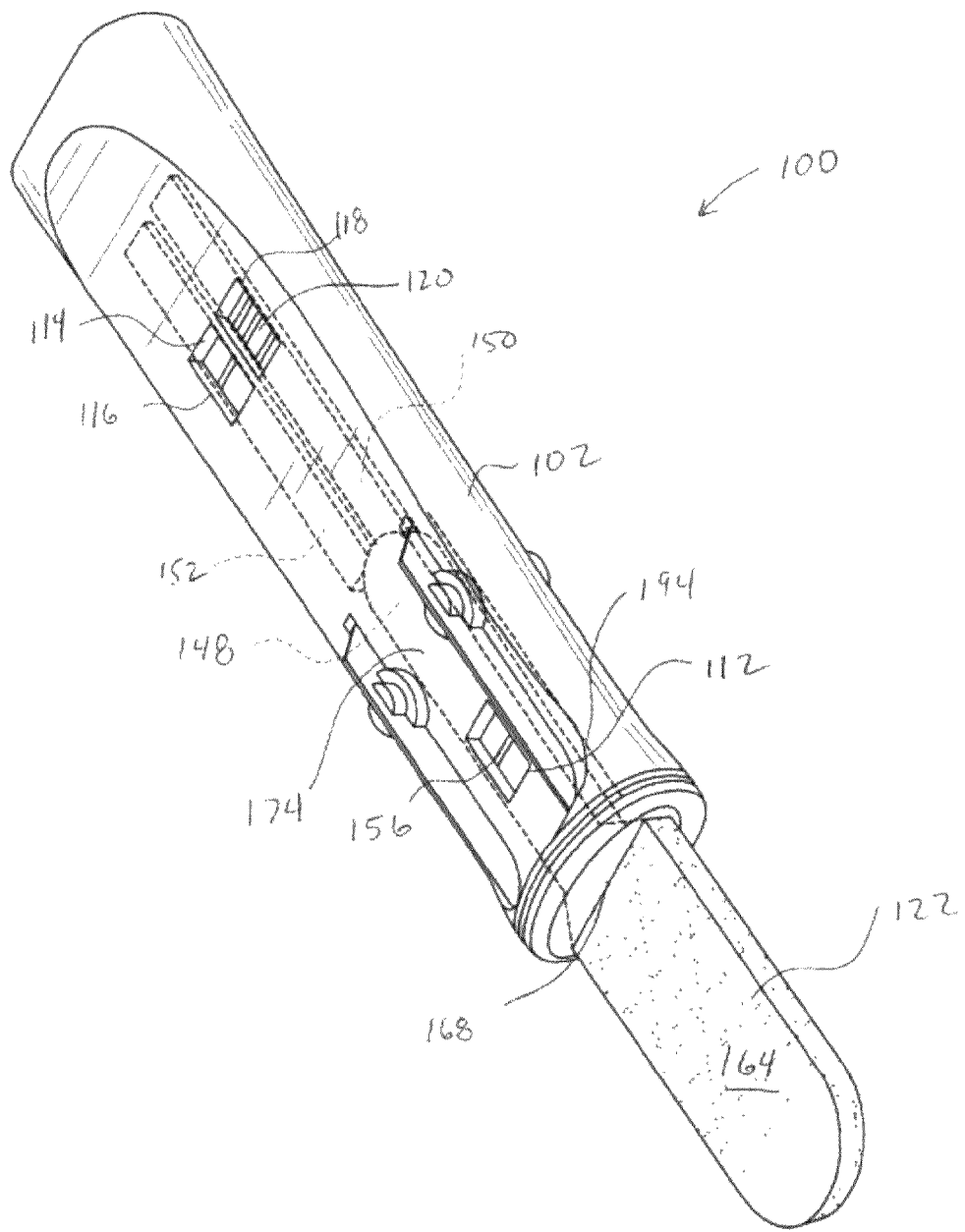
FIG. 5 is a perspective view of a sample collector of a first embodiment.
Figure 6:
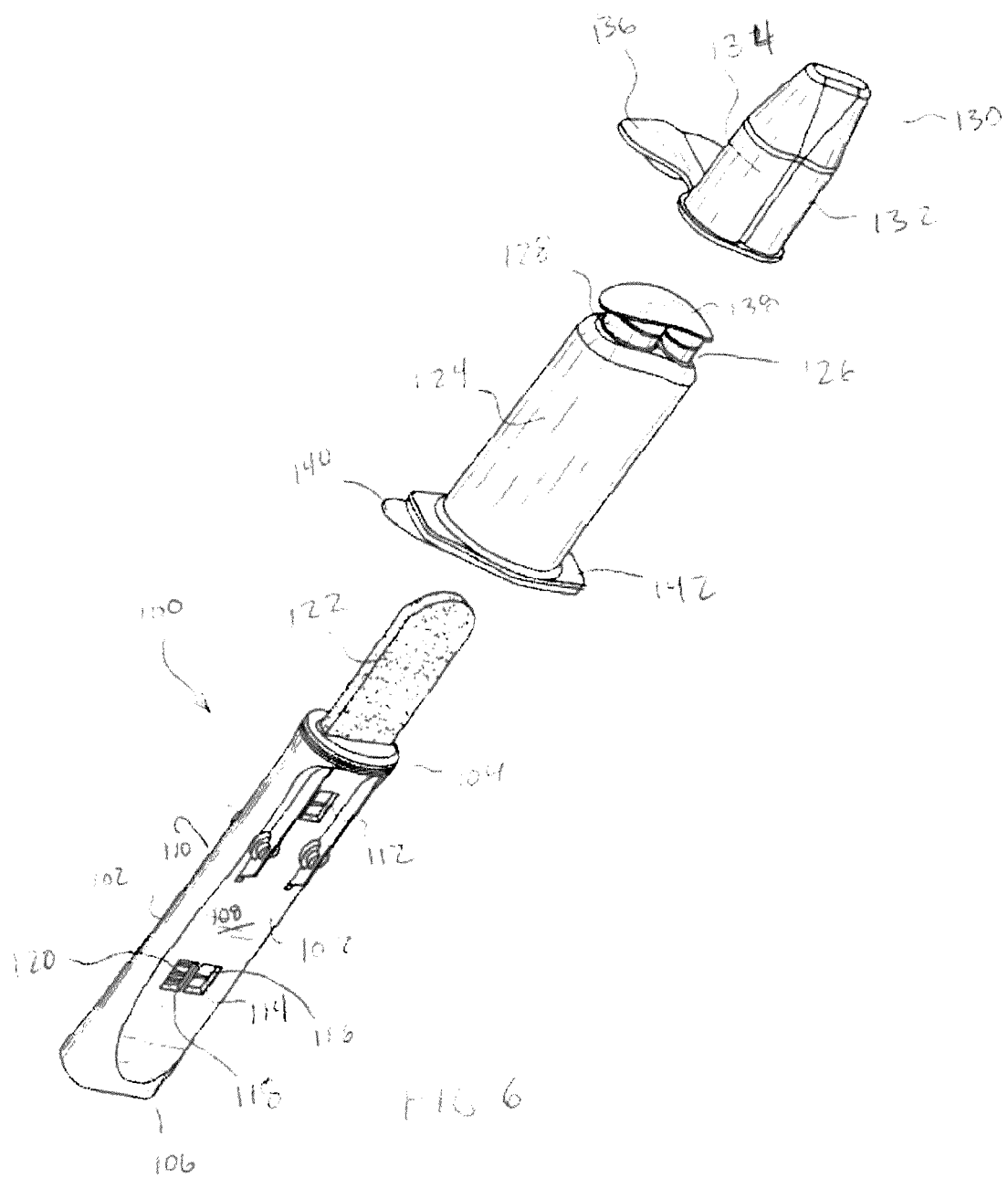
FIG. 6 is a view of a sample collector of a first embodiment.
Figure 7:
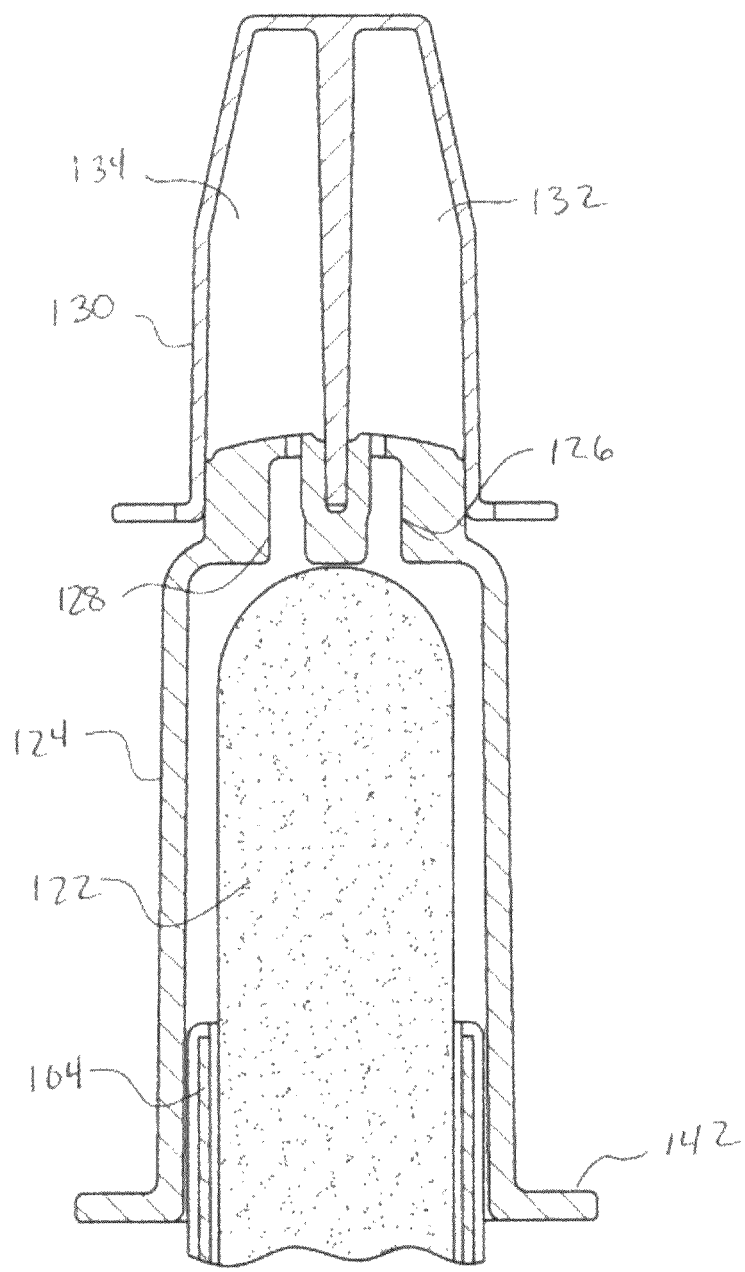
FIG. 7 is a cutaway side view of a collection tube and pad compression tube partially inserted over an absorbent pad of a first embodiment.

Referring to FIG. 5, in the first embodiment, a plurality of test strips 116 and 120 is in fluid communication with absorbent pad 122 through a membrane 194. Absorbent pad 122 includes an exposed collection portion 164 which is outside handle 102 and is inserted into the sample collection point—e.g. into a subject's mouth to collect saliva—and a tongue extension 174 contained within handle 102 which extends lengthwise to contact adequacy indicator 112 and draw sample fluid toward test strips 116, 120. Pad collection portion 164 and tongue extension 174 are joined at absorbent pad base 168. Membrane 194 is disposed parallel to and in contact with extension tongue 174 as well as test strips 116, 120, such that absorbent pad 122 maintains fluid communication with test strips 116, 120 through membrane 194. Membrane 194 is selected to wick the selected sample fluid, and provide some filtering of some undesired constituents of the sample fluid to more rapidly and evenly distribute sample fluid to test strips 116, 120.

Figure 14:
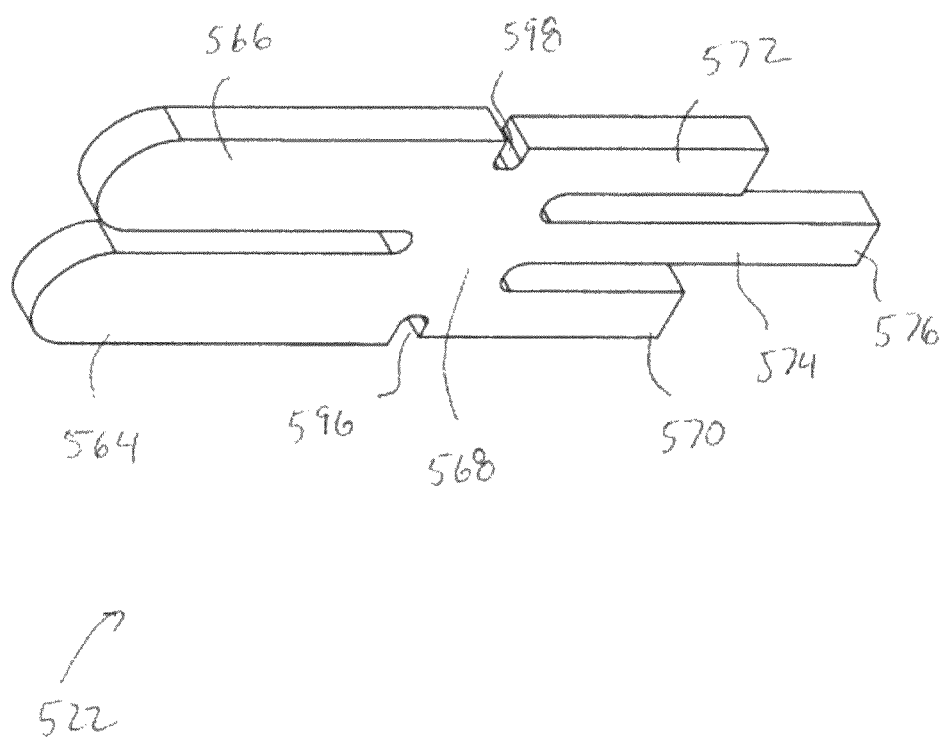
FIG. 14 is a perspective view of a double-tongue absorbent pad of an embodiment.
Figure 15:
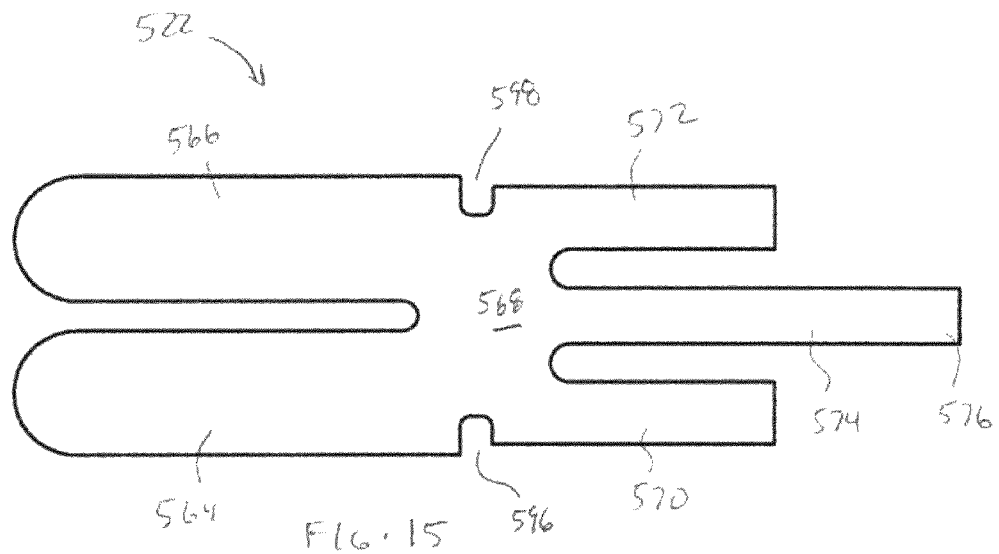
FIG. 15 is a plan view of a double-tongue absorbent pad of an embodiment.

Referring to FIGS. 13-15, a sample collector 500 of a fifth embodiment is shown. In the embodiment, sample collector 500 includes an absorbent pad 522 partially contained within handle 502, a sufficiency indicator 512 in handle 502, first and second test strips contained in handle 502 to provide observable indications of test results through first and second windows 514, 518, in handle 502, and a pad compression tube 524 to go over sample pad 522 and an end 504 of handle 502. Pad compression tube 524 includes collection tube ports 526, 528, sealingly connectable to sample collection tubes (not shown), and flange collar 542 to strengthen pad compression tube 524 and provide grips to operate it. A progressive locking mechanism is provided, including first and second projections 544 on opposing sides of handle 502 (opposite side not visible) and corresponding opposing first and second channels 546 extending lengthwise along opposing pad compression tube side walls 545, 547 (547 not visible) to frictionally engage first and second projections 544. Channels 546 also act to align and guide pad compression tube 524 as it is inserted over absorbent pad 522 and handle 502.

Again referring to FIGS. 13-15, in the fifth embodiment collector dam 586 is inserted over the absorbent pad 522 proximal to base 568 and against the handle first end 504. Collector dam 586 is in sealing contact with the absorbent pad 522 and the inside wall surface of the pad compression tube 524, and the collector dam 586 permits liquid sample to migrate along the absorbent pad 522 toward and into handle 502 during collection, but prevents flow when the absorbent pad 522 and handle 502 are inserted into the pad compression tube 524. Engagement against the interior walls compresses collector dam 586 to choke off back flow toward handle 502 to enhance the volume of sample liquid expressed by absorbent pad collection portion Still referring to FIGS. 13-15, in the embodiment absorbent pad 522 includes first and second collection portions 564, 566 to go into the sample collection area, and first second and third extension tongues 570, 572 and 574 extending into handle 502, all joined at base portion 568. First and second extension tongues extend in parallel along opposing sides within handle 502 be in fluid communication with first and second test strips 516, 520, respectively, and third extension tongue 574 extends centrally to end 576 and is in contact with sufficiency indicator 512. Collector dam 586 engages absorbent pad 522 around lateral slots 596, 598.

Referring to FIGS. 16-22, a sample collector 700 of a sixth embodiment is shown, similar to the fifth embodiment but having an absorbent pad 622 with a single collection portion 664 rather than twin portions. Absorbent pad 622 includes a collection portion 664, base portion 668, opposing lateral slots 696, 698, and first, second and third extension tongues 670, 672, and 674 extending to end 676. Sample collector 700 includes a handle 702 with opposing first and second ends 704, 706, and opposing first and second sides 708, 710. Handle 702 includes a sufficiency indicator 712—a light pipe including a spacer 758, first and second test strips 716, 720, observable through first and second windows 714, 718, on the first side 708 of handle 702 with sufficiency indicator 712. Opposing first and second protrusions 744 from handle first and second sides 708, 710, are provided to engage corresponding channels on a pad compression tube. First and second extension tongues 670, 672, are in direct contact against membranes 778, 780, respectively, to distribute sample fluid to test strips 720, 716, respectively. Reservoirs 782, 784, in contact with test strips 716, 720, absorb fluid to draw sample entirely along the length of test strips 716, 720. Collector dam 786 inserts over absorbent pad 622 to engage it around opposing lateral slots 696, 698. Collector dam tabs 788 engage with collector tab receivers 790 to retain collector dam 786 in place, which in turn retains absorbent pad 622 in place.

Referring to FIG. 17, in the embodiment collector 700 includes an area on the handle 702 proximal to the test strip windows 714, 718, to receive a optical data label 78, such that the optical data label 78 is within the imaging device 22 field of view when the sample collector handle 702 is inserted into the sample collector receiving portion 16, the optical data label 78 including sample-specific data, for example: test subject name and identification number, test procedure, date/time of test, test conductor, patient vital signs or symptoms, & etc. The optical data label 78 is inserted into the field of view in order to be recorded with the image of the test results. Additionally, the electro-optical reader 12 may include software to "read" the optical data label data 78 for instructions to run specific analytical procedures, to transmit the test specific data along with test results to a location remote from the test location, to verify identities and/or results, or for other uses. An optical data label may utilize any number of optical data formats, such as one- and two-dimensional bar codes, optical character recognition ("OCR"), dot patterns, color patterns & etc, which may be used to encode information.

Referring to FIGS. 16 and 23-28, a sample collector 800 of a seventh embodiment is shown, identical to the sixth embodiment but having only a single test strip 816 and window 814 in handle 802, rather than a plurality of test strips and windows. Absorbent pad 622 includes a single collection portion 664, base portion 668, opposing lateral slots 696, 698, and first, second and third extension tongues 670, 672, and 674 extending to end 676. Sample collector 800 includes a handle 802 with opposing first and second ends 804, 806, and opposing first and second sides 808, 810. Handle 802 includes a sufficiency indicator 812—a light pipe including a spacer 858, test strip 816 observable through window 814, on the first side 808 of handle 802 with sufficiency indicator 812. Opposing first and second protrusions 844 from handle first and second sides 808, 810, are provided to engage corresponding channels on a pad compression tube. First and second extension tongues 670, 672 is in direct contact against membrane 878 to distribute sample fluid to test strip 816. Reservoir 882, in contact with test strip 816, absorbs fluid to draw sample entirely along the length of test strip 816. Collector dam 886 inserts over absorbent pad 622 to engage it around opposing lateral slots 696, 698. Collector dam tabs 888 engage with collector tab receivers 890 to retain collector dam 886 in place, which in turn retains absorbent pad 622 in place.

Referring to FIG. 23, in the embodiment collector 800 includes an area on the handle 802 proximal to the test strip window 814 to receive an optical data label 78, in the embodiment a optical data label, such that the optical data label 78 is within the imaging device 22 field of view when the sample collector handle 802 is inserted into the sample collector receiving portion 16, the optical data label 78 including sample-specific data, for example: test subject name and identification number, test procedure, date/time of test, test conductor, patient vital signs or symptoms, & etc. The optical data label 78 is inserted into the field of view in order to be recorded with the image of the test results. Additionally, the electro-optical reader 12 may include software to "read" the optical data label data for instructions to run specific analytical procedures, to transmit the test specific data along with test results to a location remote from the test location, to verify identities and/or results, or for other uses.

Referring to FIGS. 1-7, a portable hand-held electro-optical reader 12 of a specimen sample collection device and test system 10 is shown. In the embodiment, reader 12 includes a housing 14, the housing 14 including a collector port 16 to receive a test sample collector 100 having one or more test strips 116 and 120 disposed in the collector handle 102 for giving observable indications of the presence of selected substances within a test sample, and an aperture 18 to access a data processing device touch screen 20; an imaging device 22 mounted within the housing 14, the imaging device 22 having a field of view oriented to image a selected portion of a test sample collector 100 and at least one of its corresponding test strips 116 and 120 when the test sample collector handle 102 is inserted into the port 16; an imaging processor 24 mounted within the housing 14 and in electronic communication with the imaging device 22 and data handing device 26, the imaging processor 24 to at least receive imaging data from the imaging device 22, process the imaging data for use by the data handing device 26, and transmit the imaging data to the data handling device 26; a programmable data handling device 26 removably mounted within the housing 14, the data handling device 26 including a touch screen 20, wherein the touch screen 20 is aligned with the housing aperture 18 when mounted within the housing 14.

In operation, the reader is turned on by first activating the data handling device 26. In the embodiment, data handling device 26 is a personal digital assistant (PDA/IPAQ), which incorporates software instructions stored in memory to process the test strip data. The PDA/IPAQ 26 displays prompts, such as a series of forms to be filled out by the user on touch screen 20. Each screen image guides the entry of information which may be specific to both the tester and to the test subject (or other object or substance) being tested. When this information is complete, a test screen is initialed by depressing a "button" on the touch screen 20. A sample collector 100 is placed in the collector port 16 which is designed for a specific testing sample collector or family of collectors to make it light-tight and provide proper tracking and orientation of the collector 100. The orientation of the sample collector 100 allows it to be read by the imaging device 22. In the embodiment, imaging device 22 is an electronic imager such as a charge coupled device (CCD). When the sample collector 100 is inserted into collector port 16, collector presence detector micro-switch 34 or 36 (or plurality of switches 34 and 36) is actuated by mechanical contact with collector 100, telling the logic and processing electronics that a valid collector has been detected. As an alternative arrangement, presence detector 34 may be replaced by a plurality of micro-switches, each designed to be selectively depressed by placing projection at a location selected to engage only one of the switches, for example. As another alternative, combinations of projections 76 being either omitted or present provides a capability of detecting the presence of multiple different collectors 100, since at least one of the projections must be present to assure that the presence of a sample collector is positively detected to initiate the data collection process. Alternatively, the projection(s) 76 may be replaced by small optical indicators (i.e., "dots" or "squares") which are reflective or non-reflective or of contrasting colors and micro-switches 34, 36, replaced by light source/light sensor combinations to detect reflection or non-reflection of light or of light of a given color (by providing filters in front of each light sensor). Providing three (3) reflective dots 76 provides the ability to detect seven (7) different collectors. In another alternative, magnetic switches 34, 36 could be used in conjunction with magnetic targets 76. Alternatively, optical indicators may be captured by the imaging device 22 and software employed to determine the type of sample collector 100 inserted into the collector port 16. The identification of the type of sample collector 100 is thus provided to the logic and software to perform the proper test.

The status information is conveyed to the user by flashing the test light 44. Pressing the run switch (i.e., push button) on the data handling device 26 causes the logic and processing electronics assembly to initiate operation of imaging device 22 which captures the image of the sample collector 100 including test strip(s) 116, 120, as well as optical data information provided by an optical data label 78 on the surface of the sample collector 100 adjacent to the test strip windows 116, 120. Lights 32 are provided on opposite sides of the imaging device 22 and "flash" when the test strip image is captured. In the embodiment, lights 32 emit green light to significantly enhance the sharpness of the captured image. This information is first processed by the imaging processor and then transmitted to the data handling device 26 via a special interface cable 46 (shown in part) which connects the imaging processor to the data handling device's serial input port. In the embodiment, the raw image data is transferred from imaging device 22 to data handling device 26 via an RS232 serial port configured to operate at 115,000 baud, No parity, 8 data bits, 1 stop bit. The sample collector information is examined by application specific software stored on the PDA/IPAQ and each of the tests on the sample collector 100 is "read."

Collector port 16 in housing 14 may be illuminated by an internal light source 80 mounted on the circuit board 24 to assure easy location and insertion of a sample collector 100 under low light conditions.

Light 80 may be selectively activated by depressing a small plunger 82 of a moment switch located on the side of reader housing 14. Light 80 is turned off upon release of the switch 82, or fully inserting a sample collector into collector port 16.

A polarized filter may be placed behind the lens element and the CMOS imager of imaging device 22 to reduce reflections from the surface of the plastic collector handle 102 and thereby provide image enhancement.

Figure 4:
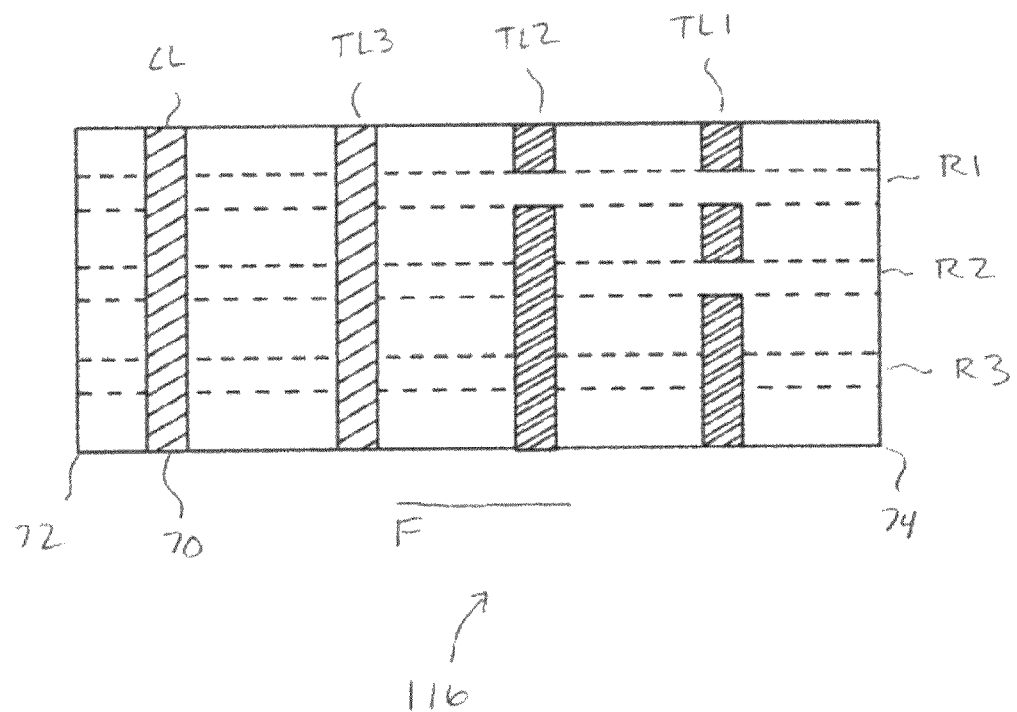
FIG. 4 is a left-side perspective view of a first embodiment of an electro-optical reader.

Referring to FIG. 4, the algorithm employed by data handling device 26 to determine the presence and type of drug (or other substance) is to scan a given area of the captured image(s) of the test strips 116, 120, to detect a line in the raw image data for a dark (i.e., low reflective) image which represents a line. The dark value area is integrated over the given area and is compared with an area adjacent to the given area which is a white or light area. If the difference of these integrated values is greater than a given threshold, a line is considered to be present. Each test strip (e.g. 116) is provided with a "Control Line" 70 (CL), which is identified as a starting point. Sample fluid flow during collection occurs in the direction from first edge 74 to second edge 72, as indicated by the "F=>". The presence of a CL is determined in accordance with the above algorithm, the position of the control line being known within a given tolerance region on either side of a "precise region", i.e., a region which the control line would occupy if the precisely aligned in the collector. The CL serves as a reference point for evaluating the test lines representing the test results. The test lines (TL1) through (TL3) and control line (CL) are parallel to one another. The lines (CL) and (TL1-TL3) are applied to the test strip 116 when manufactured and are initially invisible. The control line 70 (CL) is furthest from the right-hand end of the strip, which is the point of entry of the solution being tested. Tests for three different substances are made at spaced intervals along each test line represented by the dotted line regions (R1-R3). The control line 70 however, tests only for the presence of saliva. The movement of the saliva past control line 70 assures that the saliva has passed all of the test lines. As the solution, saliva, for example, moves toward the left-hand end of the test strip, it passes each test line, causing the "line" it passes to appear and be visible to the viewer, if the saliva does not contain the substance the test is looking for. If the substance being sought is present, as the saliva passes the first test line, (TL1), for example, the portion of test line (TL1) which intersects with region (R1) remains invisible indicating the presence of a substance being tested for and in a given percentage. Note that the portions of the test line (TL1) intersecting with regions are visible in the example shown, indicating that the substances being tested for are not present in the required amount. A different percentage amount of the substance being tested for is determined by each of the test lines (TL1-TL3). Control line 70, in addition to assuring that the saliva has passed all three test lines, also serves to precisely locate the three test lines. For example, if the test strip 116 is not precisely aligned in the sample collector or is less than the precise length when manufactured, when control line 70 is located, by the algorithm described above, the separation distances of the test lines nevertheless remain constant, and thereby enable the electronics to precisely locate each of the test lines, to compensate for a deviation from precision alignment of the test strip 116 in the collector. Positive and negative values of the test lines TL are determined relative to the control line CL. If a control line is not detected, tests on the test strip being examined are considered "Invalid." In the embodiment, the image of the test strip 116 is compressed into a standard 4-bit monochrome .bmp file, enabling data handling device 26 to display the image in a standard format.

At the completion of the test cycle (which is performed in 6-8 seconds), the results are displayed on the data handling device 26 touch screen 20 along with an image of the sample collector 100 including test strips 116, 120, and associated optical data label 78. This information, as well as the filled out test forms await signature of the tester entered by stylus 48 and are then electronically stored within the PDA/IPAQ memory. If desired, the forms and test results may also be printed by a printer 66 which communicates with the data handling device 26 over a communications link, for example a wireless BLUETOOTH® connection 68 or a cable, and/or transmitted by wireless communications means to a remote facility such as a computer server or central lab office. For example, the image of the test strip and test results may be transferred from data handling device 26 to a desktop personal computer (PC—not shown) using off-the-shelf software and hardware.

Due to the alignment requirements of the imaging device 22, an imager adjustment plate 28 is provided to allow outside adjustment of the imager during initial assembly. Imager adjustment plate 28 includes slots 30 to receive and hold imaging device 22.

Reader 12 may be charged using an AC adapter accessed through the charger access port 40. In this case, both the data handling device 26 and the imaging processor 24/imaging device 22 are charged at the same time. The state of battery charge is shown on the PDA/IPAQ display 20 as well as by flashing the charge light 42.

Test information may be downloaded from the PDA/IPAQ to a PC or other host device using a built in USB port 38.

The test results may also be sent to a printer using the USB port 38 outlet or to a wireless printer using a Bluetooth or other wireless link by pressing the print button on the data handling device 26 screen 20. Alternatively, a small printer may be incorporated into housing 14, such as a small strip printer. Upon completion of the testing sequence by the reader, the printer may automatically print a hard copy of the test results, which may be required for situations such as roadside drug testing.

Housing 14 includes first and second housing parts 56 and 58 which join to form a first interior cavity portion for mounting electronic components and a second interior cavity portion accessed by collector port 16. In the embodiment, imaging device 22, imaging processor 24, cable connector 46, and other electronics are mounted within the cavity defined by first and second housing parts 56 and 58. First housing part 56 includes a recess portion 62 oriented outward to receive a data handling device 26, for example an IPAQ PDA device. Retainer piece 60 with aperture 18 goes over data handling device 26 and removably couples to housing first part 56 to retain data handling device 26 in place. Cover plate provides customized identification of push buttons and indicator lights. Data handling device touch screen 20 aligns with aperture 18 to permit user access to touch screen 20 for operation. A transparent shield 54 may be provided, anchored in slot 52, to prevent contamination of the first interior cavity by sample collection devices inserted into collector port 16.

The arrangement and look of user screens and menus on the PDA/IPAQ screen 20 include the following:

A menu driven system is provided and includes several user selected screens to facilitate activation of specific features and provide visual and audible display and indications of the results of primary functions of the device.

An introductory screen indicating that the system is ready to use, includes:

An image capture process bar just below the center of the screen.

A battery charge level bar with the % of battery charge remaining to the right of the bar.

Four softkeys to: a) enter data on the subject under test; b) initiate a test; and c) obtain system information.

Selection of optional features such as a keypad or written entry of alphabetical or numeric characters (employing stylus 48).

A test results screen with an image display area showing the visual test results as they appear on the test strips 116, 120 (or other test strips as appropriate), including: A signature entry area for administrative signatures (by stylus 48); Results of test analysis such as pass, fail, and the nature of the substances detected. Softkeys at the bottom of the touch-screen 20 to select features such as request for a printout, information form, signature erasure, and print previews; Exiting the screen and returning to the previous screen to initiate the next test.

The physical design of reader housing is configured to adapt to many different pocket PC's or PDA devices 26.

In order to enable the reset button of the PDA (1) to be operated without having to remove the pocket PDA from the reader, a small, inconspicuous access hole is provided near the upper left-hand corner. A guide, such as a hollow cylinder is integrally molded into the housing 14 and extends inwardly toward the data handling device 26 to guide a small diameter dowel or a straightened end of a paper clip, for example, to engage and depress the reset button (not shown), enabling the operator to reset the PDA without disassembly.

Samples of the tested fluids may be retained by expressing the samples from the absorbent pad 122 using pad compression tube 124 in fluid communication with sample collection tubes 130 through collection tube ports 126, 128. Confirmation testing is therefore easily accomplished.

The use of an electro-optical reader with a reliable sample collector having multiple test strips permits more reliable testing. The test system may include multiple strips each to detect the presence of at least one substance in common between them in a single sample. By including multiple test strips indicating for the same substance, confirmation is immediate.

Alternatively, a test system may include multiple test strips each to detect the presence of different substances in a sample in order to collect maximum data.

Another alternative is that a test system may include the multiple test strips each to detect the presence of a different substance in a sample, where the different substances each provide an indication of the same condition of a test subject. Thus, testing for multiple markers of a single condition increases reliability.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

The invention claimed is:

1. A specimen sample collection device and test system comprising an electro-optical reader to receive a sample collector, the sample collector having a handle, an absorbent pad partially contained within the handle, a sufficiency indicator contained in the handle, one or more test strips contained within the handle in fluid communication with the absorbent pad, a window to observe indications on the one or more test strips from a test, and a pad compression tube insertable over the absorbent pad and at least part of the handle to express liquid sample from the absorbent pad, wherein the window remains unobscured when the pad compression tube is inserted over the handle, the electro-optical reader further comprising:

a housing including an aperture to view and operate a programmable data handling device touch screen, and a sample collector port to receive a portion of the sample collector including the window with the pad compression tube inserted over the handle;

an imaging device mounted within the housing and having a field of view oriented to image a selected portion of the sample collector inserted into the sample collector port;

an imaging processor mounted within the housing and in electronic communication with the imaging device and data handing device, the imaging processor to at least receive imaging data from the imaging device, process the imaging data for use by the data handing device, and transmit the imaging data to the data handling device;

a programmable data handling device removably mounted within the housing, the data handling device including a touch screen, wherein the touch screen is aligned with the housing aperture when mounted within the housing; and the reader further comprising a transparent anti-contamination shield within the housing disposed between the sample collector receiving port and housing interior.

* * * * *